(12) United States Patent
Weigl et al.

(10) Patent No.: US 6,557,427 B2
(45) Date of Patent: May 6, 2003

(54) CAPILLARIES FOR FLUID MOVEMENT WITHIN MICROFLUIDIC CHANNELS

(75) Inventors: Bernhard H. Weigl, Seattle, WA (US); Gerald L. Klein, Edmonds, WA (US); Ronald L. Bardell, Redmond, WA (US); C. Frederick Battrell, Redmond, WA (US)

(73) Assignee: Micronics, Inc., Redmond, WA (US)

(*) Notice: Subject to any disclaimer, the term of this patent is extended or adjusted under 35 U.S.C. 154(b) by 0 days.

(21) Appl. No.: 09/864,099

(22) Filed: May 23, 2001

(65) Prior Publication Data

US 2002/0025279 A1 Feb. 28, 2002

Related U.S. Application Data

(60) Provisional application No. 60/206,878, filed on May 24, 2000.

(51) Int. Cl.[7] .................................................. G01N 1/26
(52) U.S. Cl. .................................... 73/863.31; 73/864.72
(58) Field of Search ...................... 73/863.31, 864.72; 436/180

(56) References Cited

U.S. PATENT DOCUMENTS

| | | | |
|---|---|---|---|
| 4,849,340 A | * | 7/1989 | Oberhardt ..................... 435/13 |
| 4,946,795 A | | 8/1990 | Gibbons et al. |
| 4,989,319 A | | 2/1991 | Kapolnek et al. |
| 5,010,951 A | | 4/1991 | Kapolnek et al. |
| 5,051,146 A | | 9/1991 | Kapolnek et al. |
| 5,204,525 A | | 4/1993 | Hillman et al. |
| 5,223,219 A | * | 6/1993 | Subramanian et al. ......... 422/55 |
| 5,627,041 A | * | 5/1997 | Shartle ...................... 435/7.24 |
| 5,932,100 A | * | 8/1999 | Yager et al. ................. 210/634 |
| 5,932,315 A | * | 8/1999 | Lum et al. ................... 428/172 |
| 6,019,944 A | * | 2/2000 | Buechler ...................... 422/58 |
| 6,136,272 A | * | 10/2000 | Weigl et al. ............. 422/82.05 |
| 6,143,248 A | | 11/2000 | Kellogg et al. |
| 6,153,073 A | * | 11/2000 | Dubrow et al. ............. 204/453 |
| 6,240,790 B1 | * | 6/2001 | Swedberg et al. ........ 73/863.21 |
| 6,284,113 B1 | * | 9/2001 | Bjornson et al. ........... 204/453 |
| 2002/0025279 A1 | * | 2/2002 | Weigl et al. ................ 422/100 |

FOREIGN PATENT DOCUMENTS

| | | |
|---|---|---|
| WO | WO 9807019 A | 2/1998 |
| WO | WO 9960397 A | 11/1999 |

* cited by examiner

*Primary Examiner*—Daniel S. Larkin
*Assistant Examiner*—C D Garber
(74) *Attorney, Agent, or Firm*—Jerrold J. Litzinger

(57) ABSTRACT

A capillary for introduction of whole blood into an analysis device. The capillary has a variable volume along its length, which allows the liquid sample to be drawn into the interior of the cartridge, away from the inlet, reducing the risk of contamination of the sample from the outside.

7 Claims, 4 Drawing Sheets

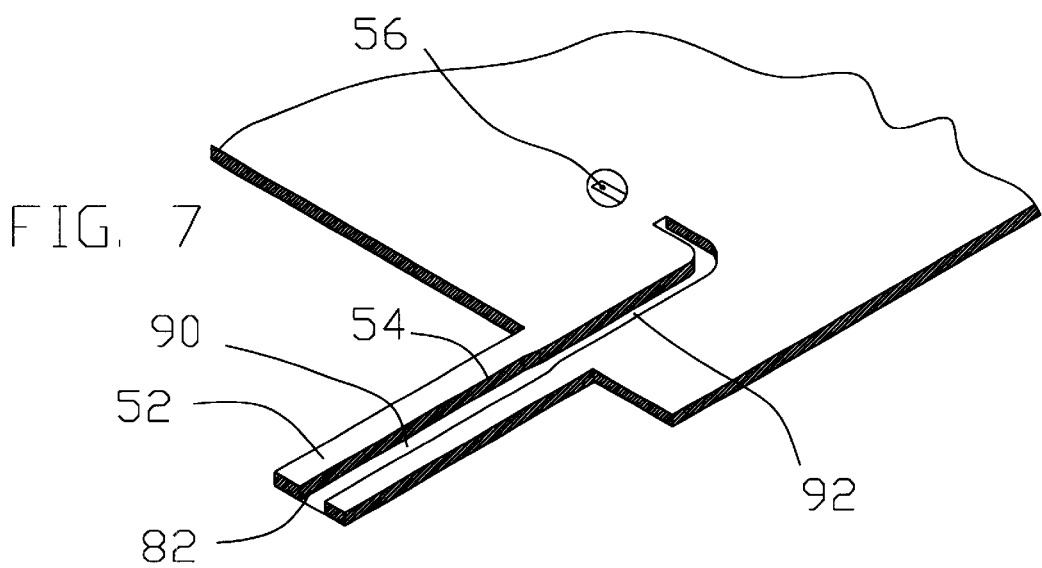
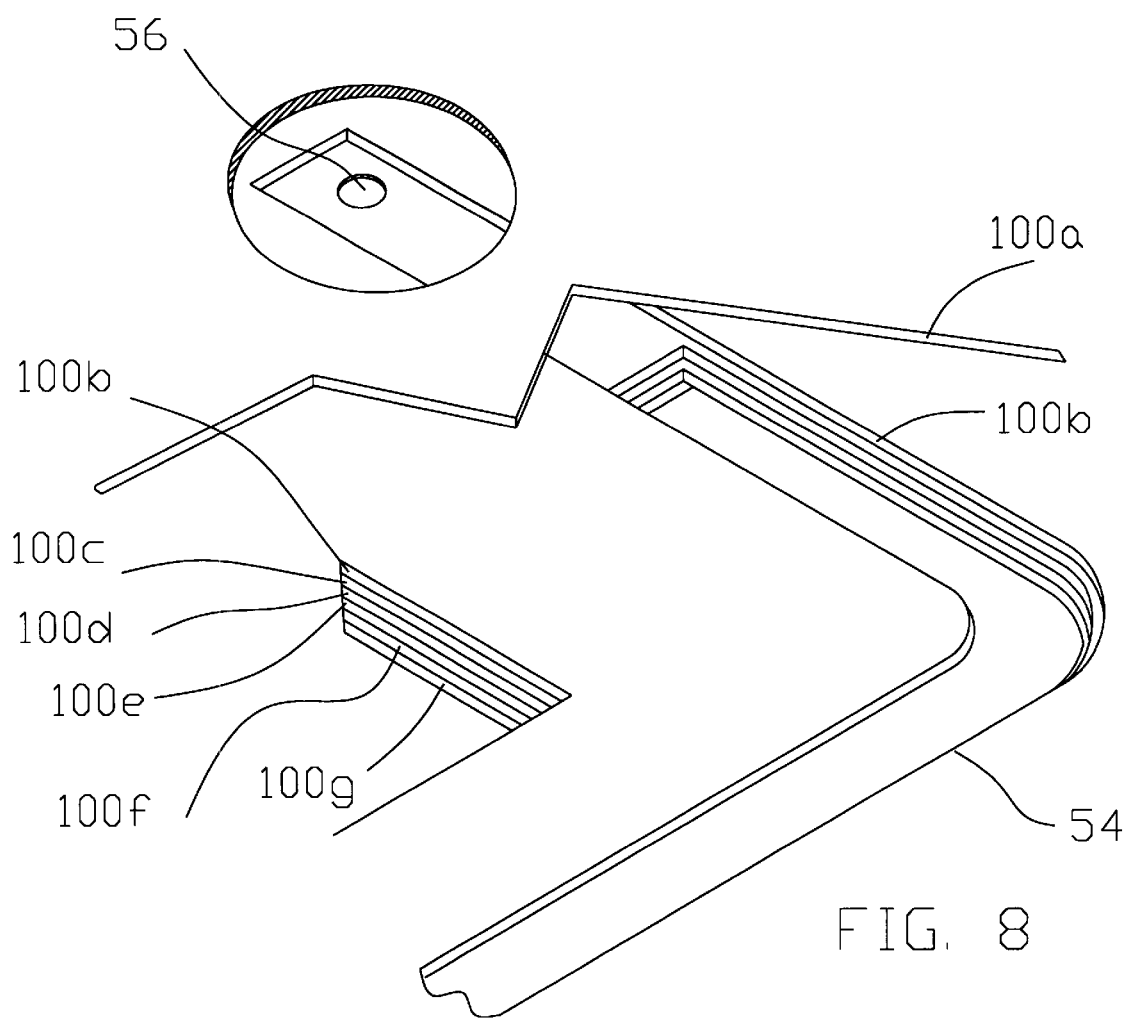

CAPILLARIES FOR FLUID MOVEMENT WITHIN MICROFLUIDIC CHANNELS

CROSS REFERENCE TO RELATED APPLICATIONS

This patent application claims benefit from U.S. Provisional Patent Application No. 60/206,878, filed May 24, 2000, which application is hereby incorporated by reference.

BACKGROUND OF THE INVENTION

1. Field of the Invention

This invention relates generally to microscale devices for performing analytical testing, and, in particular, to channels for introducing whole blood samples or the like into microfluidic circuits while reducing the risk of contamination from outside sources.

2. Description of the Prior Art

Microfluidic devices have recently become popular for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition of information for the medical field.

Microfluidic devices may be constructed in a multi-layer laminated structure where each layer has channels and structures fabricated from a laminate material to form microscale voids or channels where fluids flow. A microscale channel is generally defined as a fluid passage which has at least one internal cross-sectional dimension that is less than 1 mm and typically between about 0.1 µm and about 500 µm. The control and pumping of fluids through these channels is affected by either external pressurized fluid forced into the laminate, or by structures located within the laminate.

Capillary action is well known in the prior art for moving liquids through microchannels. This movement is defined as the movement of a liquid within the spaces of a porous material due to the forces of adhesion, cohesion, and surface tension. Microfluidic devices typically call for the use of capillary force to draw a sample into the internal chambers of the device. Such capillary flow devices, particularly capillary flow devices designed for a constant flow rate, typically include at least one capillary acting as a pump, usually for controlling the volume of a sample and the time period for reaction. U.S. Pat. No. 5,204,525, which issued Apr. 20, 1993, describes such a device. The capillaries of this device are generally of a smaller cross section or diameter in the direction transverse to the direction of flow than the chambers contained in the structure. The cross section or length in the direction of flow may be similar or may differ by a factor of ten or more, depending on the function of the capillary or chamber. Capillaries generally will have diameters in the range of about 0.01 mm, and may be 1 cm or more. Subsequent capillaries may be as long as 10 cm. The first capillary will initially control the rate of flow into the chamber.

Often, capillaries provide the sole driving source for the movement of liquid through the device. Accordingly, careful fabrication of the capillary to exact dimensions is required, and the composition of the walls is selected so as to provide the desired degree of wetting and surface tension, as the device is used without ancillary motive force.

Standard capillaries used for moving liquids in devices as described have a constant diameter which move the fluid along within the capillary to fill the channel from the opening where the fluid was applied to an area within the capillary channel. However, variable depth capillaries have been used in some instances with respect to heat transfer applications. U.S. Pat. Nos. 4,989,319; 5,010,951; and 5,051,146, which are assigned to Lockheed Missiles and Space Company, all discuss the advantages to using capillary grooves of variable cross sections on the interior surfaces of heat pipe.

A fluid plug can travel in a capillary if the surface tension at the two ends of the capillary is different. This can be achieved through conical capillaries, or by different surface treatments at different points in the capillary.

SUMMARY OF THE INVENTION

It is therefore an object of the present invention to provide a device which allows the introduction of a sample into a microfluidic analysis cartridge while reducing the risk of contamination of the sample.

It is a further object of the present invention to provide a method for completely drawing a sample into a microfluidic channel such that the fluid is no longer in contact with the entrance to the channel.

These and other objects of the present invention will be more readily apparent from the description and drawings that follow.

BRIEF DESCRIPTION OF THE DRAWINGS

FIG. 7 is a fragmentary perspective view of a microfluidic cartridge which uses the principles of the present invention;

FIG. 8 is an enlarged view of a portion of the cartridge section shown in FIG. 7;

DETAILED DESCRIPTION OF THE PREFERRED EMBODIMENTS

Figure 1:
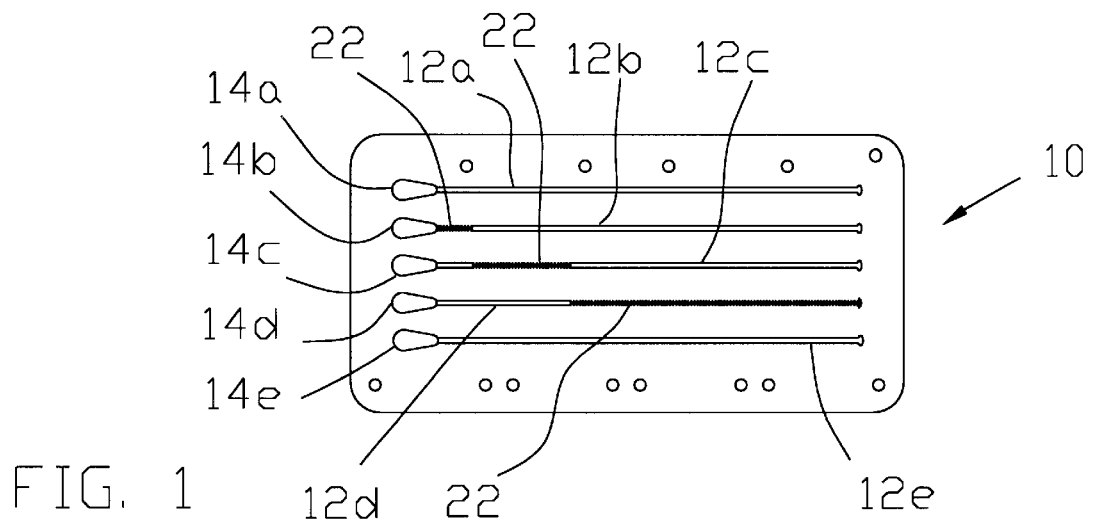
FIG. 1 is a plan view of a microfluidic cartridge illustrating the principles of the present invention.

Referring now to FIG. 1, there is shown a microfluidic card, generally indicated at 10, containing a plurality of capillaries 12a–e. Each capillary 12a–e has an associated input reservoir 14a–e for introducing a fluid into card 10. Each of reservoirs 14a–e has a capacity of approximately 30 µl.

Figure 2:
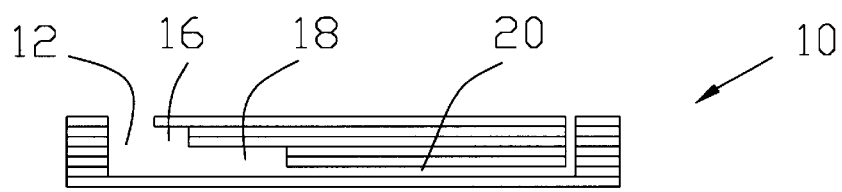
FIG. 2 is a cross-sectional view through a channel of the cartridge shown in FIG. 1.

Capillaries 12a–e each have a uniform width, but have a reduced depth along its length. First segments 16 each has a depth of 300 micrometers, second segments 18 each have a depth of 200 micrometers, while third segments 20 each have a depth of 100 micrometers, as can be seen in FIG. 2. The overall capacity of each segment is identical at approximately 15 microliters, as the length of each segment is different.

In operation, a fluid plug 22 having a volume of 15 microliters is introduced into capillaries 12d, 12c, and 12b sequentially via reservoir 14. This amount of fluid is larger than the volume of each segment 16, 18, 20 of capillary 12, thus forcing the fluid to be partially in two segments at all times. This creates an imbalance in surface tension on each side of fluid plug 22 due to the difference in channel depth along capillary 12, creating a force which propels fluid plug 22 toward thinner channel 20.

This principle can be used for fluid movement or pumping, or for introducing samples far into a microfluidic circuit such that the sample no longer has, at the end of the movement of the fluid plug, any direct contact to the outside of the microfluidic card, thus reducing the risk of contamination.

Figure 3:
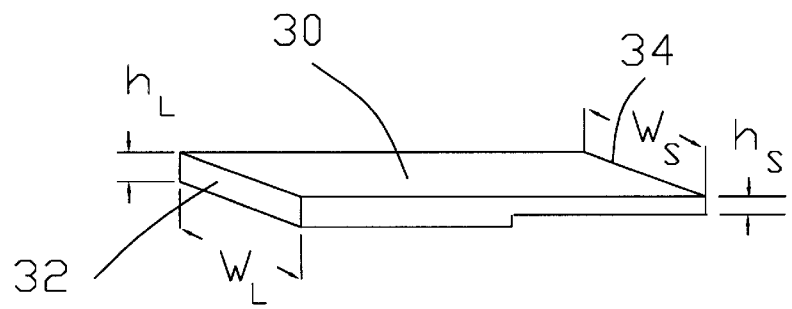
FIG. 3 is a perspective view showing the cross section of a microfluidic channel having a step decrease in the flow cross-sectional area.

FIG. 3 shows a lengthwise cross section of a microfluidic channel with a rectangular flow cross section that has a step decrease in the flow cross-sectional area. Referring now to FIG. 3, a section 30 of a microfluidic channel has a first end 32 and a second end 34. First end 32 has a width $w_L$ and a depth $h_L$, while second end 34 has a width $w_s$ and a depth $h_s$.

Figure 4:
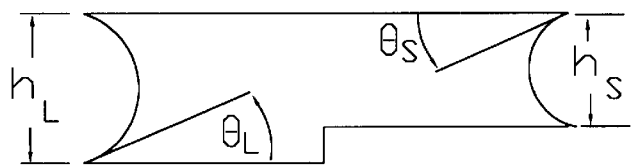
FIG. 4 is a side view of the channel of FIG. 3 showing the liquid-gas interface referenced to the liquid-solid interface in the channel.

The capillary pressure P at a liquid-vapor interface in a channel with a rectangular cross section of width w and depth h is expressed as:

$$P = 2\sigma \cos \theta (1/h + 1/w)$$

in which ay is the liquid-vapor interfacial tension ($\sigma \cos \Theta$ is sometimes referred to as the "wetting tension") and $\Theta$ is the "contact angle" that describes the liquid-vapor interface at the surface of the solid, as seen in FIG. 3. Contact angle $\Theta_L$ at the larger interface end 32 and contact angle $\Theta_s$, at the smaller interface end 34 can be seen in FIG. 4.

If there is an imbalance between the capillary pressure of each interface 32 and 34, the liquid will flow toward the direction of the largest capillary pressure, assuming equal gas pressure at both ends 32, 34 of channel 30. The imbalance of capillary pressures may be achieved by a difference in wetting tension parameters or channel width or depth. For example, if:

$$P_L = 2\sigma_L \cos \Theta_L (1/h_L + 1/w_L) < 2\sigma_s \cos \Theta_s (1/h_s + 1/w_s) = P_s$$

then the liquid will flow in the direction from interface end 32 to end 34. Note that any combination of the interface parameters may be altered to create an imbalance in the capillary pressures. A geometrically-induced imbalance could be created by a ramp or other similar geometry instead the step changes in the depth that is illustrated in FIG. 3.

The spontaneous flow of whole blood into a microfluidic channel can be employed as a means of introducing a whole blood sample into a microfluidic circuit. The penetration of a non-swelling liquid such as whole blood into a rectangular channel is described by the Lucas-Washburn equation for fluid flow in a slot structure:

$$L^2 = (R_h \sigma \cos \Theta_l)/3\zeta$$

where

L=length (cm) of penetration after time t (sec)
$R_h$=depth of channel (cm)
$\sigma$=surface tension (dyne/cm)
$\Theta$=contact angle
$\zeta$=viscosity (dyne-sec/cm)

The equation predicts rapid introduction of whole blood into a rectangular microfluidic channel whose cross-sectional dimensions are approximately 100 microns by 1,000 microns. As long as the contact angle of whole blood and the channel surface is less than 80°, then after the first second approximately 1.0 cm of the channel would have been filled, as can be seen in the graph shown in FIG. 5. This equates to about 1.0 microliters of whole blood. After five seconds, the amount of whole blood which penetrates into the microfluidic circuit would be 2.5 cm for a volume of 2.5 microliters, as can be seen in the graph shown in FIG. 6.

Figure 5:
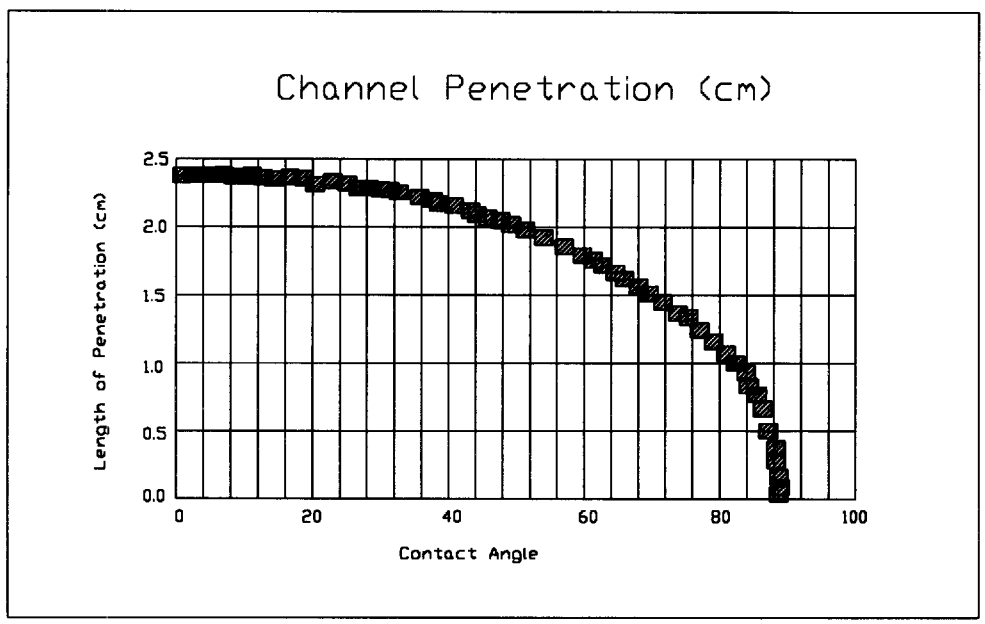
FIG. 5 is a graph showing channel penetration of a whole blood sample versus contact angle for a channel having dimensions of 100 microns by 1000 microns after 1 second.
Figure 6:
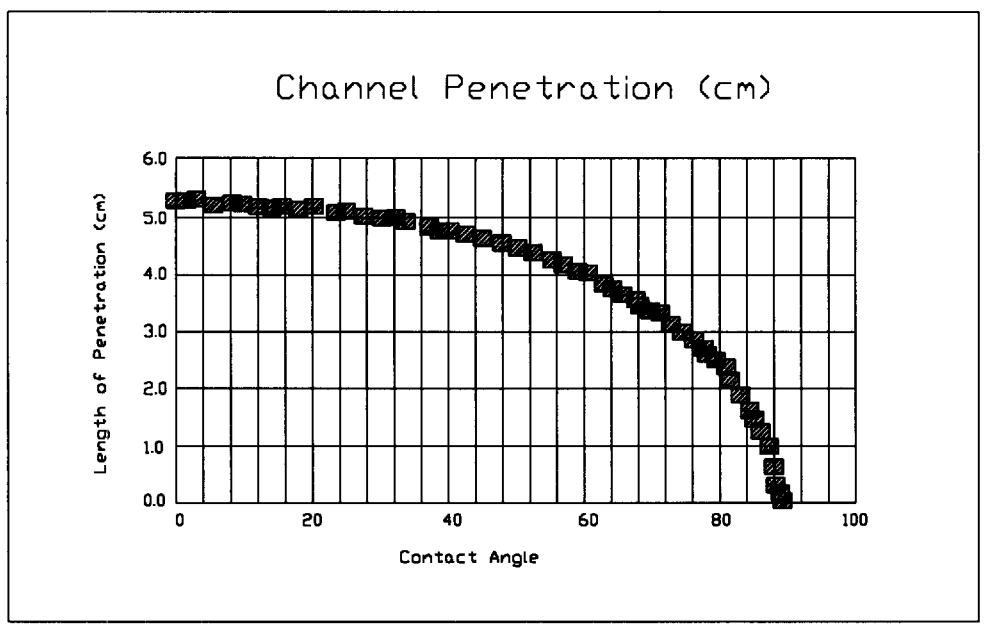
FIG. 6 is a graph showing the channel penetration of the whole blood of FIG. 5 after 5 seconds.

If the contact angle is reduced to 20 degrees by surface modification of the channel surface, then the length of penetration for 1 second and 5 seconds is 2.3 and 5.1 cm, respectively, as can be seen in FIGS. 5 and 6. This equates to 2.3 and 5.1 microliters of whole blood. By varying the channel width and depth, as well as the surface energy of the channel, one can control the amount of whole blood penetration into a microfluidic slot structure.

Figure 9:
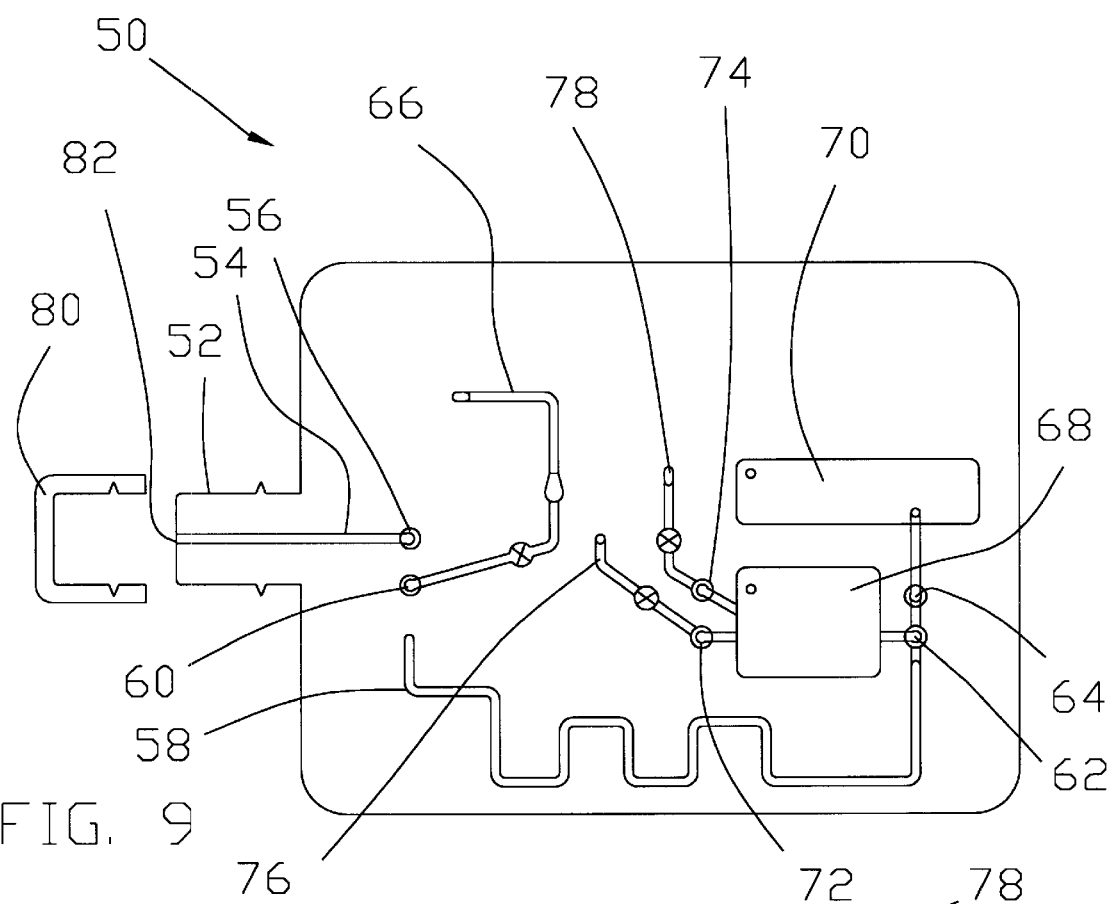
FIG. 9 is a plan view of a microfluidic analysis cartridge before the application of a whole blood sample.
Figure 10:
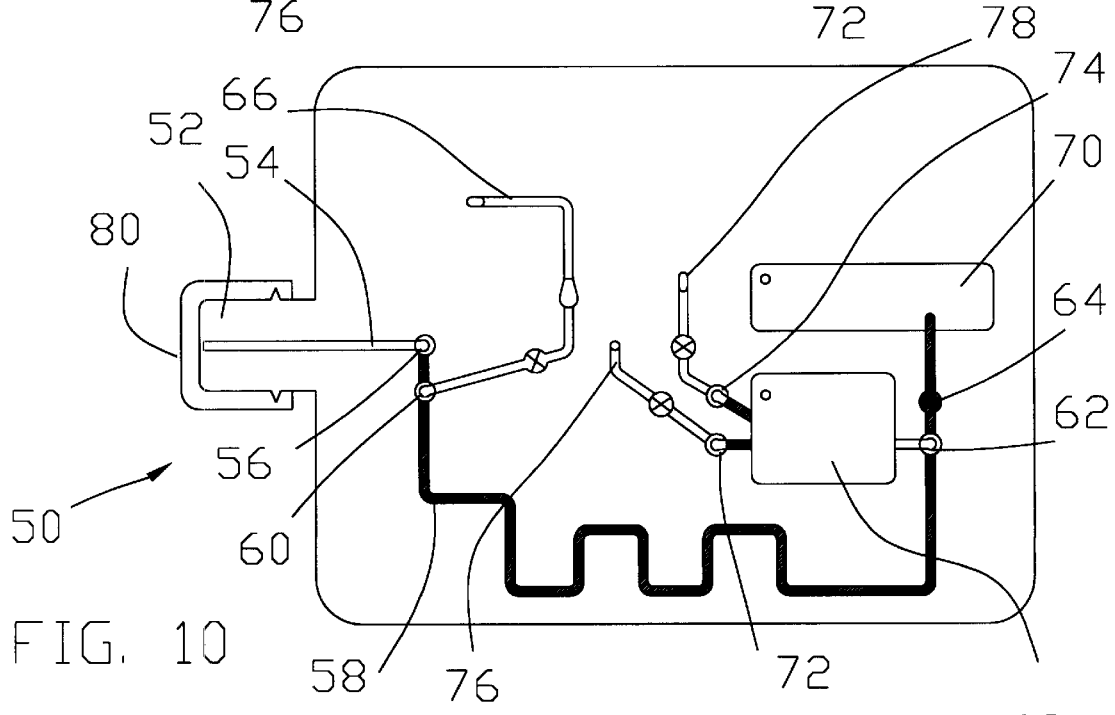
FIG. 10 is a plan view of the cartridge of FIG. 9 after application of a whole blood sample.

FIGS. 9 and 10 show a microfluidic circuit cartridge which embodies the present invention. Referring now to FIG. 9, there is shown a microfluidic cartridge, generally indicated at 50, for use in the analysis of a whole blood sample. Cartridge 50 is preferably of the type which performs a series of operations in a whole blood sample, such as lysing, hemoglobin extraction, hemoglobin measurement, red cell and platelet counting, white cell measurement, and waste storage.

Cartridge 50 contains an input section 52 for sample introduction. Section 52 is provided with a capillary 54 according to the present invention for transporting the sample to the interior of cartridge 50 for analysis. Capillary 54 terminates at a valve 56 which controls movement of the sample throughout cartridge 50. Valve 56 is also coupled to a main channel 58, which channel also intersects several other valves 60, 62, 64. Valve 60 connects channel 58 to a sample injector 66, while valve 62 connects channel 58 to a sample driver 68. Valve 64 connects channel 58 to a waste storage chamber 70. Several valves 72, 74 are used to couple sample driver 68 to sample injector 66 via channels 76, 78 respectively.

To load cartridge 50 with a sample of whole blood for analysis, a replaceable cap 80 is removed to provide access to capillary 54. At this stage, valves 56 and 64 are open, while valves 60, 62, 72, 74 are in the closed position. A drop of whole blood is placed at the end 82 of capillary 54 at inlet section 52. Capillary action draws blood into capillary 54 away from end 82 to reduce the chance that the sample may be contaminated. Cap 80 is then replaced, and cartridge inserted into a suitable test instrument for analysis. Valves 56 and 64 are then closed, while valves 60, 62, 72, 74 open, allowing whole blood to be forced into sample injector 66 by sample driver 68. Suitable aspiration means could also be used to move the sample into sample injector 66.

FIG. 7 is an enlarged fragmentary view of input section 52 and capillary 54 of cartridge 50. As can be clearly seen in FIG. 7, capillary 54 is composed of a first channel 90 and a second narrower and shallower channel 92. The reduction of volume within capillary 54 provides the imbalance of capillary pressures which causes the whole blood sample to be drawn into the interior of cartridge 50, where it is protected from possible contamination. FIG. 8 is an enlarged view of capillary 54 showing its construction within cartridge 50. Cartridge 50 is made up of a series of laminar sheets 100a–g. Sheets may be constructed from plastic or MYLAR® film or any other suitable material.

While the present invention has been shown and described in terms of several preferred embodiments thereof, it will be understood that this invention is not limited to these particular embodiments and that many changes and modifications may be made without departing from the true spirit and scope of the invention as defined in the present claims. Alternate embodiments can be used for the capillaries of the present invention. For example, variations may include conical shapes, non-stepped (smooth) transitions from large to smaller diameters, rectangular cross sections, and round or elliptical cross sections.

What is claimed is:

1. A microfluidic device, comprising:
    a first channel having an inlet opening, an outlet, and a longitudinal section between said inlet opening and said outlet, said longitudinal section having a first portion, coupled to said inlet opening, sized to generate a first capillary pressure, and a second portion, coupled between said first portion and said outlet and spaced away from said inlet opening, sized to generate a second capillary pressure greater than said first capillary pressure;
    a second channel extending away from said first channel;
    valve means, coupling said outlet of said first channel to said second channel;
    and fluid introduction means;
    wherein when a fluid plug is introduced at said inlet opening, said fluid plug is drawn into said first channel such that said fluid plug flows into said second portion of said first channel toward said valve means such that the trailing edge of said fluid plug is completely spaced apart from said inlet opening.

2. The device of claim 1, further comprising valve actuator means for controlling said valve means to selectively couple said first and second channels.

3. The device of claim 2, wherein when said valve actuator means is activated when said fluid is introduced at said inlet opening, said fluid enters said second channel from said first channel.

4. The device of claim 3, wherein fluid is contained within said second channel after said valve actuator means is deactivated.

5. The device of claim 1, wherein said fluid is whole blood.

6. The device of claim 1, wherein at least a portion of said first channel is cone-shaped.

7. The device of claim 2, wherein said valve actuator means may be actuated manually.

* * * * *